(12) United States Patent
Barnhart et al.

(10) Patent No.: US 6,267,976 B1
(45) Date of Patent: Jul. 31, 2001

(54) SKIN CLEANSER WITH PHOTOSENSITIVE DYE

(75) Inventors: Ronald A. Barnhart, Mogadore; Bradley D. Helfman, Solon, both of OH (US)

(73) Assignee: Gojo Industries, Inc., Akron, OH (US)

( * ) Notice: Subject to any disclaimer, the term of this patent is extended or adjusted under 35 U.S.C. 154(b) by 0 days.

(21) Appl. No.: 09/550,106

(22) Filed: Apr. 14, 2000

(51) Int. Cl.$^7$ .................................................. A61K 7/00
(52) U.S. Cl. ............................ 424/401; 514/844; 514/846
(58) Field of Search ..................... 424/401, 63; 514/844, 514/846

(56) References Cited

U.S. PATENT DOCUMENTS

| | | | |
|---|---|---|---|
| 4,965,063 | 10/1990 | Casey et al. ........................... | 427/7.1 |
| 5,047,167 | 9/1991 | Steyn et al. ........................... | 252/160 |
| 5,057,303 | * 10/1991 | Casey ..................................... | 424/7.1 |
| 5,064,635 | 11/1991 | Casey ..................................... | 424/7.1 |
| 5,110,492 | 5/1992 | Casey ..................................... | 252/90 |
| 5,284,603 | 2/1994 | Repinec, Jr. et al. ............... | 252/546 |
| 5,357,989 | 10/1994 | Gathani ................................. | 132/321 |
| 5,476,614 | 12/1995 | Adamy et al. ........................ | 252/544 |
| 5,607,667 | 3/1997 | Holcomb ............................... | 424/70.1 |
| 5,616,781 | 4/1997 | Sajic et al. ............................ | 510/221 |
| 5,635,462 | 6/1997 | Fendler et al. ........................ | 510/131 |
| 5,756,441 | 5/1998 | Thomas et al. ....................... | 510/235 |
| 5,929,004 | 7/1999 | Ushijima et al. ..................... | 510/100 |

* cited by examiner

Primary Examiner—Shelley A. Dodson
Assistant Examiner—Konata M. George
(74) Attorney, Agent, or Firm—Reese Taylor

(57) ABSTRACT

A cleanser product which will not stain surfaces is disclosed. Specifically, the present invention provides a cleanser comprising a photosensitive dye. The present invention also provides a method for preventing the of staining of surfaces by cleanser products.

8 Claims, 1 Drawing Sheet

Structure of F & D Red Number 28

FIGURE
Structure of F & D Red Number 28
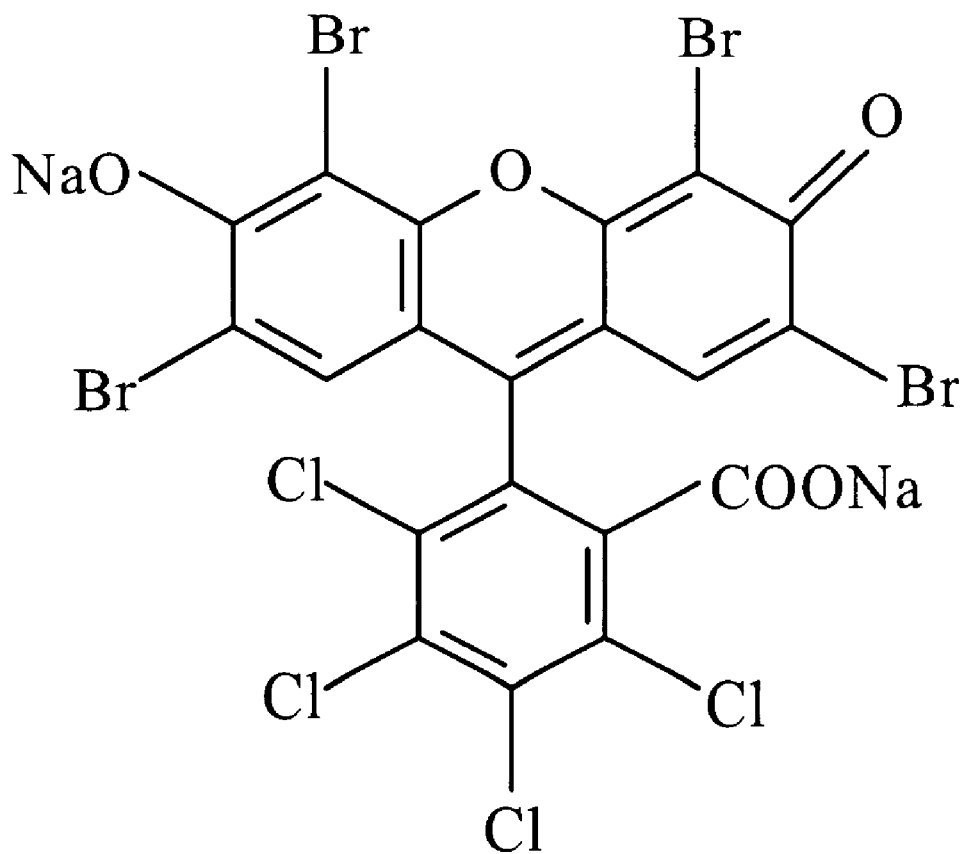

SKIN CLEANSER WITH PHOTOSENSITIVE DYE

TECHNICAL FIELD

This invention relates to a soap product for cleansing the skin. More particularly, this invention relates to a skin cleanser that does not visibly stain surfaces when left as a residue on such surfaces. Specifically, this invention relates to a skin cleanser containing a photosensitive dye that fades, or otherwise visually disappears, when it is exposed to sunlight or fluorescent light. The dye is stable, i.e., does not fade, in a light inhibited environment such as, for example, in a dispenser.

BACKGROUND OF THE INVENTION

Skin cleansing formulations are generally well known in the art and typically include one or more active cleaning agents or detergents as well as any of several known antimicrobial agents to disinfect as well as cleanse the skin, particularly the hands. Other additives commonly used in such products include surfactants, foaming agents, solvents, thickening agents, moisturizers, vitamins, fragrances, and, as discussed herein, dyes or colorants.

Skin cleaning compositions are commonly found in kitchens, bathrooms and restrooms to be applied to the hands or skin of the user to cleanse or otherwise rid or disinfect the skin of any dirt, grime or germs which may be present on the hands or skin of the user. Today, many of these skin cleansers are liquid soaps and gel-like products which are readily accessible to the user by simply pouring, spraying or otherwise dispensing the product from a dispenser or other container mounted on a wall or placed on a countertop near the sink or other wash basin. These liquid products typically are of a color and fragrance that the user will associate with cleansing or with overall good health. For example, some soap products may be orange in color and have the fragrance of a orange, thereby appealing to the user's senses as providing a fruity, healthy product to the skin. Alternatively, some liquid skin cleansers may be pink in color wherein the user may associate that the product is offering some sort of medicinal quality. Of course, other colors associated with healthy products are also often employed.

Regardless of the color and fragrance employed, users such as children often attempt to use too much skin cleanser. As a result, excess skin cleanser is released from the dispenser and deposited on any of a variety of inanimate surfaces such as counters, floors, tiles and related fixtures. These surfaces can be made from any of a variety of materials including wood, marble, stone, ceramic, formica, and other well known composite materials. Unfortunately, these surfaces usually are not the same color as the skin cleanser. Thus, cleaning personnel are often wiping the counters, tiles, and fixtures to remove the excess skin cleanser that can be clearly seen on the surface due to the differences in color.

Where the excess skin cleanser is not removed over an extended period of time, a stain or unsightly residue may result. Skin cleansing compositions often contain compounds such as dyes or colorants which, if left untreated, may leave a stain or dark residue on certain surfaces. This is especially true of surfaces beneath fixed dispensers, where excess cleanser may drip onto the surface repeatedly before being removed.

Thus, a need exists for a skin cleanser that will not leave a colored residue on surfaces if the residue is left there for any appreciable amount of time.

Akin to this problem was the problem faced by surface cleaners. In that instance, the problem was that dyes were needed in the surface cleaner to visually determine and insure that a particular surface had been contacted by the cleaner and disinfectant. If the user did not remove all of the cleaner from the surface however, a colored residue would still remain. U.S. Pat. Nos. 4,965,063, 5,110,492, 5,057,303, and 5,064,635 all describe overcoming this problem by providing a cleaning composition for surfaces having a pH sensitive dye which includes a germicide and disappears upon exposure to air. While such a pH sensitive dye might be useful in a surface cleanser, it is not particularly useful in a skin cleansing composition since the dispensers currently employed in the skin cleansing industry are typically not airtight. Thus, the dye would disappear even before it is dispensed.

Photosensitive dyes are generally known in the art. These dyes have commonly been used to determine whether a product has been exposed to light so as to warn the user of a particular hazard. Moreover, the use of these dyes typically require that the dye change from a clear, transparent state to a colored state, thereby providing a visual warning to the user. The incorporation and use of a photosensitive dye in a skin cleanser is believed, heretofore, unknown.

SUMMARY OF THE INVENTION

It is, therefore, an object of the present invention to provide a skin cleansing product containing a photosensitive dye.

It is another object of the present invention to provide a skin cleansing product, as above, that fades or otherwise disappears when exposed to light.

It is still another object of the present invention to provide a skin cleansing product, as above, that will leave no colored residue on a surface upon exposure to light.

It is yet another object of the present invention to provide a skin cleansing product that includes the aesthetic appearance desired of skin cleansing products with respect to color, but which offers a change in aesthetic appearance if not used in the skin cleansing environment.

At least one or more of the foregoing objects, together with the advantages thereof over the existing art, which shall become apparent from the specification which follows, are accomplished by the invention as hereinafter described and claimed.

In general, the present invention provides a skin cleansing composition that includes a photosensitive dye that fades rapidly when exposed to light.

The present invention also provides a method for creating a more aesthetic environment on a surface where a skin cleansing product has been deposited. The method includes providing the skin cleansing product with a photosensitive dye and exposing the skin cleansing product to natural or artificial light when present on the surface such that the color of the skin cleansing product fades and disappears.

BRIEF DESCRIPTION OF THE DRAWINGS

The FIGURE is a representation of the chemical structure of F&D Red Number 28.

PREFERRED EMBODIMENT FOR CARRYING OUT THE INVENTION

Generally, the present invention is based upon the finding that cleansers, particularly skin cleansing products, may include a photosensitive dye without affecting the skin cleaning properties of the cleanser. The present invention is therefore directed toward a composition which provides a skin cleanser product with a photosensitive dye which fades or otherwise virtually disappears upon exposure to light. The dye is light sensitive, but is stable when it is not exposed to light, such as when the cleanser is stored in a dispenser. This skin cleanser will not stain surfaces in the same manner as ordinary skin cleaning products can, because the photosensitive dye will degrade upon exposure to natural or artificial light. By the term "stain," it is meant that there is an appreciable difference in the color of the cleanser and the surface on which the cleanser has been deposited.

Dyes of the type utilized in the skin cleansing compositions of the present invention are added essentially for the aesthetic effect they create in producing a colored product, not for any cleansing properties associated therewith. Moreover, the dye is thoroughly mixed and completely dispersed in the product.

The composition can be a fluid, such as a liquid, or gel hand cleanser. When the product is delivered to the surface, as when excess cleanser drips from a dispenser, the colored composition loses color upon exposure to light, thereby preventing the visible staining of the surface. This is particularly advantageous when the cleanser is delivered from a fixed dispenser. In such a case, excess cleanser can drip onto a fixed location repeatedly. If the cleanser has a standard, non-photosensitive dye, the repeated application of the dye to one location can result in a stain on the surface to which the cleanser is applied. The present invention, however, eliminates this problem because the photosensitive dye degrades or vanishes upon exposure to natural or artificial light.

The basic cleansing product of this invention is a mixture of one or more surfactants or detergents with a photosensitive dye dispersed therein. Surfactants which may be used in the present invention include nonionic and anionic surfactants such as fatty acid soaps, natural soap, alkyl polyglucosides, ethoxylated methylglucosides and non-ionic alcohol ethoxylates. Sodium laurel sulfate and sodium laureth sulfate are preferred anionic detergents. Ionic surfactants such as partially neutralized carboxylic acids and diacids, may also be used. Zwitterionic or amphoteric surfactants such as amine oxides, phospholipids, and betaines may also be used. Essentially any type of surfactant which does not degrade the photosensitive dye and does not interfere with the photosensitivity of the dye may be used in the present invention. Mixtures of surfactants and detergents may also be used and, in fact, is preferred. The surfactant(s) should also be chosen in accord with the other optional components such as the antimicrobial compound used. As shown in U.S. Pat. No. 5,635,462 to Fendler et al., certain anionic and nonionic surfactants decrease the efficacy of some types of antimicrobial compounds. The composition of the present invention typically includes one or more surfactants at a concentration of approximately 2 to approximately 10 weight percent of the active ingredient(s). This range is typical of a hand cleanser product, but the amount of surfactant may be increased if desired or as may be necessary.

As noted hereinabove, the cleanser may also contain an effective amount of one or more anitmicrobial compounds such as substituted phenols (for example, p-chloro-m-xylenol (PCMX) or triclosan), polyoxyethylene and/or polyoxypropylene polymers, or various alcohols that may also act, if desired, as solvents. Preferred alcohols include low molecular weight aliphatic alcohols such as ethanol. When an alcohol is used, it is preferably used at a concentration of about 20 to about 65 weight percent, up to about 80 weight percent based upon the weight of the total composition. When other antimicrobial compounds are used, they are used in amounts preferably ranging from about 0.1 to about 1 weight percent of the active ingredient.

The composition may optionally comprise effective amounts of one or more supplemental ingredients such as viscosity modifiers and foaming agents, abrasives, emollients, fragrances, chelating and sequestering agents, thickeners, pearlizing agents, vitamins, preservatives, and/or moisturizers. Preferred viscosity modifiers and foaming agents, if desired or necessary, include alkylamides, especially Cocamide DEA and ammonium chloride. Preferred thickeners, if desired or necessary, include hydroxyethyl cellulose, hydroxypropyl cellulose, methyl cellulose, and carboxymethylcellulose. Ethylenediaminetetraacetic acid (EDTA) is a preferred chelating agent. A preferred pearlizing agent is glycol stearate. Other glycols may be added in order to quicken the rate of dissolution of the substituted phenol (where such an antimicrobial agent is used), as an emollient or as a humectant. There are any of a number of different and well known preservatives suitable for the composition of the present invention. One particularly known preservative is a methylchloroisothiazolinone and methylisotlhiazolinonie blend available Linder the tradename Kathon CG/ICP. Again, each of these supplemental ingredients can be used in effective amounts, typically less than 1 but up to about 1 to 2 percent by weight based upon the total weight of the composition. But the ingredients will not effect the essential nature of the invention with respect to the photosensitivity of the dye.

For optimal efficacy, the pH of the composition may be adjusted by adding an acid that is compatible with the othercomponcnts oftlhis invention. Preferred acids include citric acid, lactic acid, glycolic acid, and gluconic acid. Preferably, the pH of the composition should be between 4 and 8, and more preferably, between 5.5 and 6.5. Typically, less than 1 percent by weight of any of these acids are used to achieve the proper pH balance.

The composition may also contain skin moisturizers, such as, for example, Aloe Barbadensis Gel or vitamins, such as, for example, Vitamin E (tocopherol) or Vitamin E Acetate (tocopherol acetate). Any type of skin moisturizer, vitamin, or other supplemental ingredient which is compatible with the photosensitive dye and does not interfere with the photosensitivity of the dye may be used in the present invention, but preferably in amounts of less than 1 percent by weight.

Most importantly, the skin cleansing composition includes a dye or coloring agent which is dispersed into the skin cleansing composition in the same well known manner any other coloring agents would be added to a skin cleansing composition. Any dye or coloring agent which is photosensitive, i.e. becomes colorless upon exposure to light, can be used in accordance with the present invention. Preferably, the color of the composition is noticeable when the product is dispensed, but loses color over time with exposure to light. Moreover, once the skin cleansing composition is dispensed, it begins to degrade and the color will not return to the product, even if it is returned to a light impermeable environment. However, the chemical degradation of the preferred dye can be stopped by sealing the skin cleansing composition in the light inhibiting environment. That is, the dye will begin to change color, i.e., change from a color to a clear, invisible color, immediately upon contact with sunlight or other type of light. However, the degradation will be stopped, and thus, the fading of the color will be stopped, upon reenclosing the composition in a light inhibited environment. When the skin cleanser is dispensed again, the color will continue to fade and eventually will vanish.

One example of a suitable dye is D&C Red No. 28, which is colored but becomes colorless upon exposure to sunlight or fluorescent light. The chemical formula for D&C Red No. 28 is shown in the Figure. D&C Red No. 28, available from ffilton Davis or Warner Jenkinson, is classed chemically as a xanthene color and is certified as a color additive by the U.S. Food and Drug Administration. Another suitable photosensitive dye is Blue No. 1.

The exact manner in which this particular dye degrades in sunlight is unknown to the inventor, but the result is that, upon exposure to light, the color in the dye will fade and vanish. Like everything else in this skin cleansing composition, the amount of dye necessary is an effective amount to color the product. It will be appreciated, of course, that the more coloring agent or dye put into the composition, the longer it will take for the dye to fade and disappear. Generally, the amount of dye will range from about 0.000001 percent by weight to about 0.01 percent by weight, based upon the weight of the total composition. More preferably, a range of about 0.001 weight percent to about 0.0001 weight percent is desired.

It will also be appreciated that other non-light sensitive dyes may be used in the composition of the present invention. These dyes, such as D & C Red No. 33, are used to stabilize and balance color in the final product and are used in only effective amounts for such purposes. Importantly, if used, the amount of this dye is of such a minute concentration as compared to the photosensitive dye employed that the color of the dye will not be visible in the residue of the skin cleansing composition after the photosensitive dye has degraded. This dye is only used in an amount sufficient to stabilize and balance the color of the coloring agent and does not affect the color of the overall composition after the degradation of the photosensitive dye.

The balance of the composition is typically water so as to provide 100 percent by weight of the composition. Preferably, no alcohol-based solvent(s) is utilized, although if an alcohol is used, it must be of a type which will not materially effect the photosensitive nature of the composition. In this regard, it is known that ethanol will stabilize Red No. 28 when used at about 64 percent by weight. Furthermore, all percents by weight indicated herein are based upon the percent active composition.

The skin cleansing composition of the present invention is preferably prepared by first mixing the water, pH neutralizer (e.g., citric acid), and ammonium chloride or other similar viscosity modifier. Next, a preservative, fragrance, and chelating agent may be mixed into the moiety. A pearlizing agent is then added and mixed, followed by the detergent(s) and surfactant(s). Other ingredients may be added thereafter if necessary, but the coloring agents or dyes are preferably added last and thoroughly mixed into the resultant skin cleansing composition.

Because of the photosensitivity of the composition, it should preferably be packaged immediately after preparation in any type of light-impenecable container such as, for example a dispenser wherein the composition is complete enclosed. The composition should preferably not be exposed to light, or if it is, it should only be exposed for a very short period of time. Alternatively, instead of being stored in an opaque, light inhibiting container, it is also envisioned that the composition may be packaged in a container that blocks only a specific range of wavelengths of light to which the dye is sensitive, and thereby prevents the dye from being degraded prior to delivery. In this way, the dispenser may be clear or at least partially clear.

For purposes of this disclosure, the terms photosensitive dye and light-sensitive dye, as well as dye and coloring agent, are used interchangeably to describe a dye that degrades upon exposure to light and becomes colorless. The rate of degradation is significantly dependent upon a number of factors, including, inter alia, the amount of light to which the composition is exposed, the amount of dye employed, and the composition of the dye itself. However, it is preferred that the dye in the composition degrade rapidly. By the term "rapidly" it is meant that, in normal sunlight (natural) or fluorecent (artificial) light, the majority of the color of the composition will have faded within 24 hours of exposure. More preferably, the color will have faded by at least about 80 percent after 24 hours of light exposure.

In order to demonstrate the practice of the present invention, the following examples have been prepared and tested as described in the General Experimentation section hereinbelow. The following examples should not be viewed as limiting the scope of the invention. The claims will serve to define the invention(s).

GENERAL EXPERIMENTATION

A hand cleanser was formulated using the ingredients listed in Table 1 according to the following protocol. First, water, citric acid, and ammonium chloride were mixed for 15 minutes. Next, a preservative (Kathon CG/ICP), together with a fragrance and tetrasodium EDTA (Versene 100), were mixed for into the solution for another 15 minutes. A pearlizing agent, Quick Pearl II, containing sodium laureth sulfate and glycol stearate, was then added and mixed in the solution for 10 minutes. The mixer was then turned off, and a blend of detergents and surfactants were then mixed into the solution. The mixer was used a at 60 percent blend rate. Additional cocamide DEA was added and the entire mixture was mixed for an additional 15 minutes. Finally, D&C Red No. 28 dye and D&C Red No. 33 dye were added to the mixture to colorize the composition and the entire composition was mixed for an additional 30 minutes. The resultant skin cleansing composition had a pH of 6.56 and a viscosity of about 7200 cps to 7400 cps. The composition was then dispensed into various light inhibiting containers as set forth hereinbelow wherein, through a series of experiments, the skin cleansing composition was exposed to either natural or artificial light and observed for fading of the dye after varying periods of time.

TABLE I

HAND CLEANSER FORMULATION

| Ingredient | Formula Percent Raw Material | Active Percent | INCI Name |
| --- | --- | --- | --- |
| Process Water | 82.49455 | — | Water |
| Detergent/Surfactant Blend | 15.00 | 1.89 | Sodium Laureth Sulfate |
| | | 1.74 | Cocamide DEA |
| | | 1.54875 | Sodium Lauryl Sulfate |
| | | 0.42 | Soyamidopropyl Betaine |
| Pearlizing Agent | 1.00 | 0.21 | Sodium Laureth Sulfate |
| | | 0.12 | Glycol Sterate |
| Viscosity Modifier | 0.75 | 95% active | Ammonium Chloride |

TABLE I-continued

HAND CLEANSER FORMULATION

| Ingredient | Formula Percent Raw Material | Active Percent | INCI Name |
|---|---|---|---|
| Additional Detergent/Surfactant | 0.50 | 100% active | Cocamide DEA |
| Chelating Agent | 0.10 | | Tetrasodium EDTA |
| pH Neutralizer | 0.08 | 100% active | Citric Acid-Fine Granular |
| Preservative (Kathon CG/ICP) | 0.05 | 1.15% active | Methylchloroiso-thiazolinone |
| | | 0.35% active | Methylisothiazolinone |
| Fragrance | 0.025 | — | Fragrance |
| Photosensitive Dye | 0.0004 | 100% active | D&C Red No. 28 |
| Photosensitive Dye | 0.00005 | 100% active | D&C Red No. 33 |

EXAMPLE 1

In a first experiment, four samples (1–4) of skin cleansing composition were exposed to natural light and three samples (5–7) were exposed to fluorescent light, while one sample (No. 8) remained in darkness as a control. The samples exposed to daylight, i.e., sunlight, were placed in clear containers having no protection (Sample Nos. 1 and 4), a partially transparent sleeve (Sample No. 2) wherein the sample was approximately 60 percent protected, but was slightly exposed at the top and bottom of the container, and an opaque F & B label (Sample No.3) wherein the sample was approximately 75 percent protected but was slightly exposed at the top and bottom. The samples were placed in an east-facing window, exposed to the light, and observed for fading after 3 hours and 8 hours. These samples were exposed to natural light on a day when the conditions varied from sunny for the first hour to overcast/hazy for the remainder of the day.

In a similar fashion, the samples exposed to fluorescent light were placed in clear containers having no protection (Sample No. 5), a partially transparent sleeve (Sample No. 6) and an opaque F & B label (Sample No. 7) approximately 18 inches from two 40-Watt fluorescent bulbs and were observed for fading after 3, 8, 24 and 48 hours. The results of these experiment are summarized in Table II. The amount of fading noted in each of the trials made hereinbelow was a subjective approximation based upon the routine experience of the observer(s).

TABLE II

COLOR FADING PROPERTIES OF SAMPLE COMPOSITIONS

| Sample number | Conditions | Protection | Duration | Results |
|---|---|---|---|---|
| 1 | Daylight Exposure | None | 3 hours | 90% Faded |
| | | | 8 hours | 99% Faded |
| 2 | Daylight Exposure | Sleeve | 3 hours | 90% Faded |
| | | | 8 hours | 99% Faded |
| 3 | Daylight Exposure | F & B Label | 3 hours | 90% Faded |
| | | | 8 hours | 99% Faded |
| 4 | Daylight Exposure | None | 3 hours | 90% Faded |
| | | | 8 hours | 99% Faded |
| 5 | Fluorescent Light Exposure (at 18 inches) | None | 3 hours | 0% Faded |
| | | | 8 hours | 25% Faded |
| | | | 24 hours | 80% Faded |
| | | | 48 hours | 99% Faded |
| 6 | Fluorescent Light Exposure (at 18 inches) | Sleeve | 3 hours | 0% Faded |
| | | | 8 hours | 25% Faded where exposed |
| | | | 24 hours | 50% Faded where exposed |
| | | | 48 hours | 75% Faded where exposed |
| 7 | Fluorescent Light Exposure (at 18 inches) | F & B Label | 3 hours | 0% Faded |
| | | | 8 hours | 0% Faded |
| | | | 24 hours | 1% Faded |
| | | | 48 hours | 5% Faded where exposed |
| 8 | Total Darkness (control) | None | 48 Hours | 0% Faded |

As shown in Table II the samples having no protection faded rapidly (majority less than 8 to 24 hours) under both natural and artificial light conditions. The enclosed with the sleeve faded just as rapidly as the unprotected samples in direct sunlight, but did not fade as rapidly under fluorescent light. The samples utilizing the F&B label also faded rapidly in direct sunlight, but was even less faded then the sample containing the sleeve protection. Nevertheless, there was some fading, particularly where the sample was exposed. The sample kept in total darkness did not fade or lose its color.

EXAMPLE 2

Other skin cleanser samples were subjected to different light sensitivity testing. In this example, samples of the skin cleanser were packaged in either white 2 oz. PVC bottles (Sample Nos. 9–12) or clear PVC bottles, some (Sample Nos. 15 and 16) of which had a 3 ½"×1 ½" black opaque, stock label with rounded corners attached to them, and exposed to direct sunlight, indirect sunlight (shade), or flourescent light at 18 inches for two 40 watt bulbs. The results of this test are shown in Table III.

TABLE III

LIGHT SENSITIVITY PROPERTIES OF SAMPLE COMPOSITIONS

| Sample number | Conditions | Protection | Duration | Results |
|---|---|---|---|---|
| 9 | Direct sunlight | White PVC bottle | 1.5 hours | No change |
| | | | 8.5 hours | Very faded |
| 10 | Direct sunlight | White PVC bottle | 1.5 hours | No change |
| | | | 8.5 hours | Very faded |
| 11 | Indirect sunlight (shade) | White PVC bottle | 1.5 hours | No change |
| | | | 9 hours | No noticeable change |
| 12 | Indirect sunlight (shade) | White PVC bottle | 1.5 hours | No change |
| | | | 9 hours | No noticeable change |
| 13 | Fluorescent Light Exposure (at 18 inches) | Clear PVC bottle | 1.5 hours | No change |
| | | | 25 hours | 95% Faded |
| 14 | Fluorescent Light Exposure (at 18 inches) | Clear PVC bottle | 1.5 hours | No change |
| | | | 25 hours | 95% Faded |
| 15 | Indirect sunlight (shade) | Clear PVC bottle with label | 1.5 hours | Slight change |
| | | | 9 hours | 80% Faded |

TABLE III-continued

LIGHT SENSITIVITY PROPERTIES OF SAMPLE COMPOSITIONS

| Sample number | Conditions | Protection | Duration | Results |
|---|---|---|---|---|
| 16 | Indirect sunlight (shade) | Clear PVC bottle with label | 1.5 hours 9 hours | Slight change 80% Faded |

Upon review of Table III, it will be appreciated that the white PVC bottle had an effect on the light sensitivity of the samples where they were subjected to indirect sunlight (shade). While the samples in white PVC bottles in direct sunlight faded rapidly, the white PVC bottled samples placed in indirect sunlight did not. However, the samples in the clear PVC bottles did fade in indirect sunlight and under flourescent lighting, even with labels attached.

In light of these finding, the transmittance characteristics of the white PVC bottles used are set forth in Table IV hereinbelow.

TABLE IV

PROPERTIES OF WHITE PVC BOTTLES

| Wavelength (nm) | Transmittance % |
|---|---|
| 320 | 0.1 |
| 350 | 3.1 |
| 400 | 22.8 |
| 450 | 43.0 |
| 500 | 19.2 |
| 550 | 39.1 |
| 600 | 49.1 |
| 650 | 34.9 |
| 700 | 66.8 |
| 750 | 57.3 |
| 800 | 55.5 |
| 850 | 53.5 |
| 900 | 53.6 |
| 950 | 30.1 |
| 1000 | 22.7 |
| Minimum Absorbance | 704 nm(0.172) |
| Maximum Absorbance | 320 nm(1.999) |

EXAMPLE 3

In this experiment, samples of the present invention were exposed to light from a solar simulator (Sample Nos. 17–20), direct sunlight (Sample Nos. 21–24), or fluorescent light (Sample Nos. 25–32). Samples exposed to fluorescent light were either not protected (29–32) or protected in a sleeve (25–28) as described in Example 1. A solar simulator is a device developed and engineered to deliver the same intensity and wavelength of light in 1 hour as would 24 hours of sun exposure to a particular site. The results of this experiment are summarized in Table V. Again, the amount of fading noted was a subjective approximation.

TABLE V

COLOR FADING UNDER DIFFERING TYPES OF LIGHT

| Sample number | Conditions | Protection | Duration | Results |
|---|---|---|---|---|
| 17 | Solar Simulator | None | 1 hour | Exposed area 70% faded |
| 18 | Solar Simulator | None | 1 hour | Exposed area 80% faded |
| 19 | Solar Simulator | None | 1 hour | Exposed area 80% faded |

TABLE V-continued

COLOR FADING UNDER DIFFERING TYPES OF LIGHT

| Sample number | Conditions | Protection | Duration | Results |
|---|---|---|---|---|
| 20 | Solar Simulator | None | 1 hour | Exposed area 70% faded |
| 21 | Direct sunlight | None | 0.5 hours | 95% Faded |
| 22 | Direct sunlight | None | 0.5 hours | 95% Faded |
| 23 | Direct sunlight | None | 0.5 hours | 80% Faded |
| 24 | Direct sunlight | None | 0.5 hours | 80% Faded |
| 25 | Fluorescent Light Exposure (at 18 inches) | Sleeve | 24 hours | 70% Faded |
| 26 | Fluorescent Light Exposure (at 18 inches) | Sleeve | 24 hours | 90% Faded |
| 27 | Fluorescent Light Exposure (at 18 inches) | Sleeve | 24 hours | 80% Faded |
| 28 | Fluorescent Light Exposure (at 18 inches) | Sleeve | 24 hours | 80% Faded |
| 29 | Fluorescent Light Exposure (at 18 inches) | Sleeve | 24 hours | 70% Faded |
| 30 | Fluorescent Light Exposure (at 18 inches) | Sleeve | 24 hours | 90% Faded |
| 31 | Fluorescent Light Exposure (at 18 inches) | Sleeve | 24 hours | 80% Faded |
| 32 | Fluorescent Light Exposure (at 18 inches) | Sleeve | 24 hours | 80% Faded |

Upon review of Table V, it will be appreciated that the colored compositions faded under both natural or artificial light.

EXAMPLE 4

Next, two samples (Nos. 33 and 34) of the composition ofthe present invention were exposed to fluorescent light and natural sunlight, respectively, with the protection of titanium dioxide suspended in the formula to reflect and adsorb the light. The results of this test, depicted in Table VI, show that, while the titanium dioxide had some affect on the rate of fading, the color of the composition still faded rapidly. For example, Sample No.34 showed slow or moderate fading as compared to other trials shown above, but both samples substantially degraded after 72 hours and 2.5 hours respectively.

TABLE VI

FADING WITH TITANIUM DIOXIDE

| Sample number | Conditions | Protection | Duration | Results |
|---|---|---|---|---|
| 33 | Fluorescent Light (at 18 inches) | Titanium Dioxide | 72 hours | Sample faded toward direction of light, change noticeable within 24 hours. ~80% change. |
| 34 | Direct Sunlight | Titanium Dioxide | 2.5 hours | Slow/moderate fading, ~95% change. |

EXAMPLE 5

Finally, in order to evaluate the photosensitivity of the dye of the present composition, two samples of competing products (Sample Nos. 36 and 37) which do not have a photosensitive dye were exposed to direct sunlight and examined for loss of color. These samples were then compared with a sample of the present invention. Sample No. 36 is available from Betco as Winning Hands Hand Cleanser #11219. Sample No. 37 is available from Kutol as Soft & Silky Pink Lotion Skin Cleanser #5665. Although the exact formulations of the Betco and Kutol products are believed to be confidential and the intellectual property of those manufacturers, it is known that neither of the product contain a photosensitive dye. The results of this light exposure study are summarized in Table VII. Again, the amount of fading noted was a subjective approximation.

TABLE VII

LIGHT EXPOSURE STUDY FOR THREE SKIN CLEANSERS

| Sample number | Conditions | Protection | Duration | Results |
|---|---|---|---|---|
| 35 (present invention) | Direct Sunlight | None | 2.5 hours | Rapid fading, ~99% change. |
| 36 (Betco) | Direct Sunlight | None | 3.5 hours | No noticeable change. |
| 37 (Kutol) | Direct sunlight | None | 3.5 hours | No noticeable change. |

The present invention shows rapid loss of color after 2.5 hours of exposure to direct sunlight whereas previously known cleansers do not show any appreciable loss of color after 3.5 hours of exposure to sunlight.

Thus, it should be evident that the present invention is highly effective in providing a cleanser with a photosensitive dye which will not stain surfaces and will degrade or vanish, at least from the visible spectrum, upon exposure to natural or artificial light. The invention is particularly suitable for hand cleansers which are to be dispensed from dispensers encasing the composition in darkness, but is not necessarily limited thereto, it being understood that other dispensers or other skin cleansers may be used.

Based upon the foregoing disclosure, it should now be apparent that the present invention will carry out the objects set forth hereinabove. It is, therefore, to be understood that any variations evident fall within the scope of the claimed invention and thus, the selection of specific component elements can be determined without departing from the spirit of the invention herein disclosed and described. In particular, the skin cleansing compositions of the present invention are not necessarily limited to the particular dyes set forth herein, any photosensitive dye suitable for the purposes of the present invention falling within the scope of the present invention. Thus, the scope of the invention shall include all modifications and variations that may fall within the scope of the attached claims.

What is claimed is:

1. A skin cleansing composition comprising a photosensitive dye that fades rapidly when exposed to light.

2. The composition of claim 1, wherein said skin cleansing composition is a hand cleanser.

3. The composition of claim 1, wherein said skin cleansing composition is one of a liquid or gel.

4. The composition of claim 1, wherein said skin cleansing composition is of a visible color and is placed in and dispensed from a light restrictive container.

5. The composition of claim 1, further comprising at least one detergent, at least one surfactant and at least one antimicrobial agent.

6. The composition of claim 5, further comprising at least one additive selected from the group consisting of a foaming agent, a moisturizer, an emollient, a viscosifier or thickening agent, a chealating or sequestering agent, a humcetant, a pearlizing agent, a vitamin, and a fragrance.

7. The composition of claim 1, wherein the photosensitive dye is a xanthene colorant.

8. A method for creating a more aesthetic environment on a surface where a skin cleansing product may be deposited, the method comprising:

providing the skin cleansing product with a photosensitive dye; and exposing the skin cleansing product to natural or artificial light when present on the surface such that the color of the skin cleansing product fades and disappears.

* * * * *